(12) United States Patent
Choi et al.

(10) Patent No.: US 7,456,293 B2
(45) Date of Patent: Nov. 25, 2008

(54) SUBSTITUTED CARBOXYLIC ACID DERIVATIVES FOR THE TREATMENT OF DIABETES AND LIPID DISORDERS, THEIR PREPARATION AND USE

(75) Inventors: Yong Moon Choi, Pinebrook, NJ (US); Hunwoo Shin, Livingston, NJ (US); Palanichamy Ilankumaran, Pinebrook, NJ (US)

(73) Assignee: SK Holding Co., Ltd, Seoul (KR)

( * ) Notice: Subject to any disclaimer, the term of this patent is extended or adjusted under 35 U.S.C. 154(b) by 0 days.

(21) Appl. No.: 11/391,031

(22) Filed: Mar. 28, 2006

(65) Prior Publication Data

US 2006/0281802 A1  Dec. 14, 2006

Related U.S. Application Data

(60) Provisional application No. 60/666,133, filed on Mar. 29, 2005.

(51) Int. Cl.
*A61K 31/4184* (2006.01)
*C07D 235/04* (2006.01)

(52) U.S. Cl. .................. 548/310.1; 514/394
(58) Field of Classification Search ........... 548/310.1
See application file for complete search history.

(56) References Cited

U.S. PATENT DOCUMENTS 5,314,880 A * 5/1994 Whittaker et al. .......... 514/80

FOREIGN PATENT DOCUMENTS

| WO | WO 97/28149 | 8/1997 |
|---|---|---|
| WO | WO 03072102 | 9/2003 |
| WO | WO 2004046119 | 6/2004 |
| WO | WO 2005021540 | 3/2005 |

OTHER PUBLICATIONS

Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Curtis et al., The Journal of the American Board of Family Practice, vol. 18, pp. 37-43, (2005).*
A feature Based Pharmacophore for *Candida albicans* MyristoylCo A: Protein N-Myristoyltransferase Inhibitors, Eur. J. Med. Chem., vol. 36 pp. 147-163 (2001).
H. Shinkai et al., Drugs Future, 1999, 24. (8), 893-898.
Dawn A. Brooks et al., J. Med. Chem., 2001, 44, 2061-4.
W.R. Oliver et al., PNAS, v. 98, 99. 5306-5311, 2001.
The International Search Report and Written Opinion of the International Searching Authority, issued on Jul. 10, 2007, in the PCT application No. PCT/KR2006/001152.

* cited by examiner

*Primary Examiner*—Laura L. Stockton (57) ABSTRACT

The present invention is concerned with racemic or enantiomerically enriched substituted carboxylic acids and derivatives thereof represented by Formula 1;

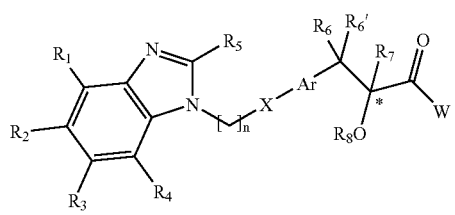

Formula 1 or pharmaceutically acceptable salts thereof. The present invention also includes pharmaceutical compositions comprising an effective amount of a compound of Formula 1 in admixture with a pharmaceutically acceptable carrier or excipient. The compositions may include additional therapeutic agents for combination therapy. The present invention provides a new class of pharmaceutically active compounds, which are useful in the treatment and control of diabetes and its related metabolic diseases.

37 Claims, 3 Drawing Sheets

Effect of Example 1 on OGTT in db/db Mice

FIG. 3

SUBSTITUTED CARBOXYLIC ACID DERIVATIVES FOR THE TREATMENT OF DIABETES AND LIPID DISORDERS, THEIR PREPARATION AND USE

RELATED APPLICATIONS

This application is a continuation of and claims priority to U.S. Provisional Application Ser. No. 60/666,133, filed Mar. 29, 2005.

FIELD OF THE INVENTION

The invention described here is concerned with the treatment and control of non-insulin dependent diabetes mellitus (type II diabetes) and its related vascular disease as well as obesity and lipid disorders.

BACKGROUND OF THE INVENTION

Diabetes refers to a disease wherein glucose level is maintained above normal range (>126 mg/dl at fasting status), or hyperglycemia, due to the malfunction of body homeostasis for various reasons. In the United States alone, 6.2% of the population (17 million) suffers from diabetes, which has many complications associated with the macro and micro vascular disease such as coronary heart disease, stroke, hypertension, neuropathy, nephropathy, or retinopathy. According to the American Diabetes Association, adults with diabetes have 2-4 times higher death rate of heart disease and chance of stroke. Each year, 12,000-24,000 people lose their sight and 30,000 people lose one or both lower limbs due to diabetes. Control of blood glucose level significantly decreases the morbidity and complications related with diabetes.

There are two types of diabetes. Type I is a disease in which the body does not produce insulin due to the destruction of β-cells and Type II is a disease in which the body does not fully utilize insulin due to the increased insulin resistance thereto. Over 90% of diabetes patients are type II.

A common treatment of diabetes is the administration of sulfonylurea drugs, such as glyburide and glimepiride, to stimulate pancreatic β-cells to produce more insulin which compensates for insulin resistance. Long term use of these insulin secretagogues, however, results in the eventual exhaustion of the β-cells and induction of more resistance at the end. Acute hypoglycemia due to temporal excess of insulin is another adverse effect of these drugs.

Biguanides, such as Metform and Phenformin, increase insulin sensitivity to a certain extent but lactic acidosis, nausea and diarrhea are reported as adverse effects to their use.

TZD (thiazolidinedione) type drugs are a more recent addition to the market. They are known to enhance insulin sensitivity by stimulation of PPARγ, peroxisome proliferators activated receptor γ, which is critical for adipocyte differentiation and the modulation of genes involved in energy storage and utilization. TZD drugs are reported to markedly enhance insulin sensitivity and obviate the occurrence of hypoglycemia, but some of them have serious liver toxicity issues. This caused Rezulin to be withdrawn from the US market in 2000. Currently, researchers are actively seeking non-TZD based drugs to avoid the liver toxicity potentially associated with the thiazolidinedione functional group. PPARα is reported to be involved in β-oxidation of the fatty acids. Ligands of PPARα, such as clofibrate and fenofibrate, are known to reduce triglyceride and LDL significantly. Since diabetes is often accompanied by obesity, dyslipidemia, atherosclerosis and high levels of LDLs which worsen the complications, efforts have been made to discover PPARα and PPARγ dual agonists which may correct the abnormalities of blood glucose and dyslipidemia at the same time. Examples of such dual agonists include JTT-501 (H. Shinkai et al, *Drugs Future,* 1999, 24), 2-methyl-2{4-[2-(5-methyl-2-aryloxazol-4-yl)ethoxy] phenoxy} propionic acid (Dawn A. Brooks et al, *J. Med. Chem.,* 2001, 44, 2061-4).

Activation of PPAR δ has been demonstrated to increase HDL levels (Leibowitz, WO97/28149, August 1997). More recently, a PPAR δ selective agonist was reported to have shown a dose-related increase in serum HDL-C and concomitant decrease in LDL-C and VLDL-TG in insulin-resistant, middle-aged rhesus monkeys (W. R. Oliver et al., PNAS, v. 98, pp. 5306-5311, 2001). Activation of PPAR δ alone or in combination with the simultaneous activation of PPARα and/or PPARγ may be desirable in formulating a treatment for hyperlipidemia in which HDL is increased and LDL is lowered.

The present invention is concerned with the general structure of Formula 1, which is a new class of compounds that do not belong to the typical structure of PPARα, PPARβ/δ and PPARγ class compounds, yet which are effective in lowering blood glucose, insulin, triglycerides, fatty acids and cholesterol, and increasing HDL. Compounds of Formula 1 below have potential as a new class of drugs that has beneficial effects over current drugs and candidate materials.

SUMMARY OF THE INVENTION

The present invention is directed to substituted carboxylic acids and derivatives thereof represented by Formula 1

Formula 1 or pharmaceutically acceptable salts thereof wherein $R_1$ through $R_8$, n, X, Ar, W are as defined below and the asterisk denotes an asymmetric carbon atom. The present invention also includes pharmaceutical compositions comprising an effective amount of a compound of Formula 1 in admixture with a pharmaceutically acceptable carrier or excipient. The present invention is an advance in the art since it provides a new class of pharmaceutically active compounds, which are useful in the treatment and control of diabetes and its related metabolic diseases. The compounds of the present invention may be in the form of the racemic mixture, or as an enantiomer in the substantial absence of the other enantiomer. The (S) enantiomers are preferred.

In biological assays, compounds of Formula 1 showed marked reduction of glucose, insulin, free fatty acids in db/db mice, thus are expected to exert similar effects in humans which may be applicable for the treatment and control of diabetes, obesity, atherosclerosis, vascular inflammation and their related diseases. Also, in cholesterol fed rats, compounds represented by Formula 1 showed reduction of total cholesterol and triglycerides as well as elevated HDL levels.

BRIEF DESCRIPTION OF THE FIGURES

The invention is further illustrated by the accompanying Figures in which.

DETAILED DESCRIPTION OF THE INVENTION

In accordance with the present invention, there are provided compounds represented by Formula 1

Formula 1

Wherein: $R_1$, $R_2$, $R_3$ and $R_4$ are independently selected from hydrogen, hydroxy, halogen, nitro, $C_{1-7}$ alkyl, $-OC_{1-7}$ alkyl, $C_{1-7}$ haloalkyl, $-OC_{1-7}$ haloalkyl, $-SO_2C_{1-7}$ alkyl, $-SO_2NR_aR_b$, $-SO_2$phenyl, $-OSO_2C_{1-7}$ alkyl, $-C(O)C_{1-7}$ alkyl, $-CO$phenyl and phenyl, wherein the phenyl groups are unsubstituted or substituted with 1-3 substituents independently selected from halogen, $-C_{1-7}$ alkyl, $-C_{1-7}$ haloalkyl, $-OC_{1-7}$ alkyl, and $-OC_{1-7}$ haloalkyl; or adjoining pairs of $R_{1-4}$, together with that portion of the ring to which they are attached, may form a partially saturated or unsaturated 5-8 member cyclic ring containing from 0-4 heteroatoms independently selected from N, O and S, said ring being unsubstituted or independently substituted with 1-3 halogens and 1-4 $C_{1-7}$ alkyl groups. Preferred groups represented by $R_1$, $R_2$, $R_3$, and $R_4$ are independently selected from hydrogen, chloro, fluoro, $-CF_3$, $-CF_2CF_3$, $C_{1-4}$ alkyl, $C_{1-4}$ haloalkyl, $-SO_2Me$ and phenyl which is unsubstituted or substituted with 1-3 substituents independently selected from halogen, methyl, ethyl, propyl, isopropyl, methoxy, ethoxy n-propoxy, isopropoxy, $-CF_3$ and $-OCF_3$. More preferably, $R_1$, $R_2$, $R_3$, and $R_4$ are independently selected from the group consisting of hydrogen, fluoro, $-CF_3$ and $-SO_2Me$;

$R_5$ is selected from hydrogen, $C_{1-7}$ alkyl, $-OC_{1-7}$ alkyl, $-O$phenyl, $-SO_2C_{1-7}$ alkyl, $-SO_2$ phenyl, $-C(O)C_{1-3}$ alkyl, $-C(O)$phenyl, $-C(O)OC_{1-3}$ alkyl and $-C(O)NR_aR_b$, wherein the phenyl groups are unsubstituted or substituted with one to three substituents independently selected from halogen, $-C_{1-7}$ alkyl, $-C_{1-7}$ haloalkyl, $-OC_{1-7}$ alkyl and $-OC_{1-7}$ haloalkyl. Preferably, $R_5$ is selected from the group of hydrogen, methyl, ethyl, $CF_3$, $CF_2CF_3$, methoxy, phenoxy, $-SO_2Me$, $-SO_2Ph$, $-COMe$, and $-C(O)Ph$, wherein the phenyl groups are unsubstituted or substituted with 1-3 substituents independently selected from halogen, methyl, ethyl, propyl, isopropyl, methoxy, ethoxy n-propoxy, isopropoxy, $-CF_3$ and $-OCF_3$. More preferably, R5 is $-CF_3$, or $-CF_2CF_3$;

$R_6$ and $R_6'$ are independently selected from hydrogen, halogen, $C_{1-7}$ alkyl, $-C_{1-7}$ haloalkyl, hydroxy, $-OC_{1-7}$ alkyl, $-OC_{1-7}$ haloalkyl and phenyl, wherein the phenyl group is unsubstituted or substituted with one to three substituents independently selected from halogen, $-C_{1-7}$ alkyl, $-C_{1-7}$ haloalkyl, $-OC_{1-7}$ alkyl and $-OC_{1-7}$ haloalkyl. $R_6$ and $R_6'$ are preferably selected from the group of hydrogen, fluoro, methyl, ethyl, phenyl, methoxy and ethoxy, most preferably hydrogen.

$R_7$ is selected from hydrogen, halogen, $C_{1-7}$ alkyl, $C_{1-7}$ haloalkyl and phenyl wherein the phenyl group is unsubstituted or substituted with one to three substituents independently selected from halogen, $-C_{1-7}$ alkyl, $-C_{1-7}$ haloalkyl, $-OC_{1-7}$ alkyl and $-OC_{1-7}$ haloalkyl. $R_7$ is preferably hydrogen, fluoro, methyl, ethyl and phenyl, most preferably hydrogen;

$R_8$ is selected from hydrogen, $C_{1-7}$ alkyl, $C_{1-7}$ haloalkyl and phenyl wherein the phenyl group is unsubstituted or substituted with one to three substituents independently selected from halogen, $-C_{1-7}$ alkyl, $-C_{1-7}$ haloalkyl, $-OC_{1-7}$ alkyl and $-OC_{1-7}$ haloalkyl. $R_8$ is preferably $C_{1-7}$ alkyl, $-C_{1-7}$ haloalkyl or phenyl, most preferably ethyl, isopropyl, $-CH_2CF_3$ or phenyl;

Ar, as it appears as a divalent linking group in Formula I, is a 6-10 membered monocyclic or bicyclic ring system that is unsubstituted or substituted with 1-5 substituents independently selected from halogen, $C_{1-7}$ alkyl, $C_{1-7}$ haloalkyl, $-OC_{1-7}$ alkyl, $OC_{1-7}$ haloalkyl and phenyl wherein the phenyl group is unsubstituted or substituted with one to three substituents independently selected from halogen, $-C_{1-7}$ alkyl, $-C_{1-7}$ haloalkyl, $-OC_{1-7}$ alkyl and $-OC_{1-7}$ haloalkyl. The divalent ring system represented by Ar is preferably unsubstituted or substituted with from 1-5 substituents independently selected from the group consisting of halogen, methyl, ethyl, propyl, methoxy, ethoxy, propoxy and $-OCF_3$;

X is a divalent linking group selected from $=O$, $=CR_aR_b$, $=NR_a$, $=CO$, $=S$ and $=SO_2$, wherein $R_a$ and $R_b$ are as defined below;

n is an integer from 1-6;

the asterisk denotes an asymmetric carbon atom; and

W is selected from the group of consisting of hydroxy, $-OR_c$, $-NR_cR_d$ and $-NR_cSO_2R_e$ wherein each of $R_c$ and $R_d$ is independently selected from hydrogen, $C_{1-7}$ alkyl and $C_{1-7}$ haloalkyl and $R_e$ is selected from hydrogen, $-C_{1-7}$alkyl, $-C_{1-7}$haloalkyl and phenyl wherein the phenyl group is unsubstituted or substituted with one to three substituents independently selected from halogen, $-C_{1-7}$alkyl, $-C_{1-7}$haloalkyl, $-OC_{1-7}$alkyl and $-OC_{1-7}$ haloalkyl. W is preferably selected from the group of hydroxy, methoxy, ethoxy, amino, $-NHMe$, $-NMe_2$, $-NHSO_2Me$ and $-NHSO_2Ph$.

Set forth below are definitions of the radicals represented by various symbols, such as $R_{1-8}$, X, Ar and W, in Formula 1.

The term "alkyl" means a straight- or branched-chain hydrocarbon radical having 1-7 carbon atoms. Non-limiting examples of suitable alkyl groups include methyl, ethyl, n-propyl, n-butyl, sec-butyl, iso-butyl, tert-butyl, n-pentyl, n-hexyl, and the like.

The term "haloalkyl" means a straight- or branched-chain hydrocarbon radical having 1-7 carbon atoms and substituted with from 1-7 halogen atoms. Non-limiting examples of haloalkyl groups include fluoromethyl, trifluoromethyl, pentafluoroethyl, heptafluoropropyl, 2,2,2-trifluoroethyl and the like.

The term "aryl" means mono- or bicyclic aromatic rings containing only carbon atoms. Aryl groups that are substituents herein are 6-10 membered monocyclic or bicyclic ring systems and are preferably phenyl or naphthyl. Phenyl is most preferred. The term also may describe an aryl group fused to another ring.

The term "halogen" includes fluorine, chlorine, bromine, and iodine. Preferred halogens are chlorine and fluorine.

A preferred group of compounds in accordance with the present invention are compounds wherein W is hydroxy, $R_6$ and $R_6'$ are hydrogen, Ar is phenyl, X is oxygen, at least three of $R_1$ through $R_4$ are hydrogen and the other is hydrogen, halogen, —$CF_3$ or phenyl, $R_5$ is —$CF_3$ or —$CF_2$—$CF_3$, $R_8$ is lower alkyl or —$CH_2$—$CF_3$ and n is 2.

The compounds of the present invention may be in the racemic form, but are preferably in an enantiomerically enriched form. By enantiomerically enriched is meant that one enamtiomer of the compounds represented by Formula 1 is present in the substantial absence of the other. By substantial absence is meant that the enriched isomer is at least about 95%, preferably at least about 97% and most preferably about 99% of the enantiomeric mixture. The (S) enantiomer of the compound of Formula 1 is preferred. In general, It should be noted that the stereochemistry of the final products of formula 1 depends on the stereochemistry of the novel intermediate amino compound to be described below, an amino intermediate enriched to the (2S) enantiomer yields a corresponding enriched carboxylic acid and an amine intermediate enriched with the (2R) enantiomer yields a corresponding enriched carboxylic acid.

The term "composition" is intended to encompass a product comprising the active ingredient (s), and the inert ingredient(s) that make up the carrier, as well as any product which result directly or indirectly, from combination, complexation or aggregation of any two or more of the ingredients, or from the dissociation of one or more of the ingredients, or from other types of reactions or interactions of one or more of the ingredients. Accordingly, the composition of the present invention encompasses any composition made by admixing a compound of the present invention and a pharmaceutically acceptable carrier.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, iron, lithium, magnesium, manganese, potassium, sodium, zinc and the like. Particularly preferred are the ammonium, calcium, magnesium, potassium and sodium salts. Salts derived from pharmaceutically acceptable organic non-toxic bases include salts of primary, secondary, tertiary amines, substituted amines including naturally occurring substituted amines such as arginine, betaine, caffeine, choline and the like. When the compound of the present invention is basic, salts may be prepared from pharmaceutically acceptable non-toxic acids, including inorganic and organic acids. Such acids include acetic, benzensulfonic, benzoic, camphorsulfonic, citric, fumaric, gluconic, glutamic, hydrochloric, hydrobromic, lactic, maleic, malic, mandelic, methansulfonic, mucic, nitric, pamoic, phosphoric, succinic, sulfuric, tartaric, p-toluenesulfonic and the like. Particularly preferred acids are citric, hydrobromic, hydrochloric, maleic, phosphoric, sulfuric and tartaric acids. It will be understood that, as used herein, references to the compounds of Formula 1 are meant to also include the pharmaceutically acceptable salts.

The class of compounds herein does not contain a 1,3-thiazolidinedione moiety which chartacterizes a number of known antidiabetic compounds. It is therefore considered unexpected that the subject compounds demonstrated strong blood glucose lowering effect in db/db mice. The subject compounds also demonstrated good fatty acid lowering effect as well. Therefore, the compounds of the present invention are considered to have good potential for the treatment and control of diabetes or its related disease such as hyperglycemia, neuropathy, nephropathy, retinopathy, obesity and also hyperlipidemia or its related disease like atherosclerosis, inflammatory condition. The present invention includes compounds having the structure of Formula 1 and its pharmaceutically acceptable salts, admixtures of compounds of Formula 1 in pharmaceutically acceptable carrier and prodrugs of these compounds.

The compounds of the present invention as represented by formula 1 are effective in lowering glucose, free fatty acid, LDL, VLDL and triglyceride, and increasing HDL. Also the subject compounds showed markedly reduced insulin and glucose amount (Auc) in the ITT (insulin tolerance test) and OGTT (oral glucose tolerance test), which are the typical phenomena observed with insulin sensitizing compounds. Therefore, the subject compounds are expected to be effective in the treatment and control of non-insulin dependent diabetes mellitus and its related complications such as nephropathy, neuropathy and retinopathy (NIDDM) in humans as well as in the treatment and control of obesity and its related disease such as hyperlipidemia, dyslipedemia, hyper-cholesterolemia, hypertriglycemia and atherosclerosis.

A preferred group of compounds in accordance with this invention are represented by Formula 2:

Formula 2 wherein $R_1$, $R_2$, $R_3$ and $R_4$ are independently selected from the group consisting of hydrogen, $C_{1-7}$ alkyl, halogen, —$OC_{1-3}$ alkyl, —$OC_{1-5}$ haloalkyl and phenyl which is unsubstituted or substituted with 1-3 groups independently selected from halogen, $C_{1-5}$ alkyl, $C_{1-5}$ haloalkyl, —$OC_{1-3}$ alkyl and —$OC_{1-3}$ haloalkyl, or adjoining pairs of $R_{1-4}$, together with that portion of the ring to which they are attached, form a partially saturated or unsaturated 5-8 member cyclic ring containing 0-4 heteroatoms independently selected from N, O and S, said ring being unsubstituted or substituted with 1-3 halogens or 1-4 $C_{1-7}$ alkyl groups; $R_5$ is selected from the group consisting of —$CF_3$, —$CF_2CF_3$, —$SO_2Me$. —COMe and —$CO_2Me$; $R_8$ is selected from the group consisting of methyl, ethyl, n-propyl, iso-propyl, and —$CH_2CF_3$ and * represents an asymmetric carbon atom. Another preferred group of compounds in accordance with the present invention are represented by Formula 3:

Formula 3 wherein $R_1$ through $R_4$ are independently selected from the group consisting of hydrogen, $C_{1-7}$ alkyl, halogen, $C_{1-5}$ haloalkyl and phenyl which is unsubstituted or substituted with 1-3 groups independently selected from halogen, $C_{1-5}$ alkyl, $C_{1-5}$ haloalkyl, —$OC_{1-3}$ alkyl and $C_{1-5}$ haloalkyl, with the proviso that at least two of $R_1$ through $R_4$ are hydrogen; $R_5$ is selected from the group consisting of —$CF_3$, —$CF_2CF_3$, —$SO_2Me$, —$COMe$ and —$CO_2Me$; and $R_8$ is selected from the group consisting of methyl, ethyl, n-propyl, iso-propyl, and —$CH_2CF_3$, and $R_8$ is selected from the group consisting of methyl, ethyl, n-propyl, iso-propyl, and —$CH_2CF_3$; and * represents an asymmetric carbon atom. It is preferred that the compounds represented by Formulae 2 and 3 are in the form of their enriched (S) enantiomers.

Synthetic Methods

The invention also relates to a method of preparing the above-mentioned compounds. The compounds of Formula 1 and 2 above can be prepared as described below. The process for preparing compounds of Formula 1 and 2, as well as preparations containing them are further illustrated in the following examples, which are not to be construed as limiting.

1. By carrying out an alkylation reaction between structure 2 wherein Y is a leaving group such as chloro, bromo, methane sulfonate or p-toluene sulfonate, and structure 3 where $R_{1-8}$, X, Ar and W are defined previously using $K_2CO_3$, or $Cs_2CO_3$ in DMF, DMSO, or acetonitrile. DEAD is diethyl azodicarboxylate.

2. By carrying out an alkylation reaction between structure 1 wherein Y is a leaving group such as chloro, bromo, methane sulfonate or p-toluene sulfonate, and structure 4 where $R_{1-8}$, X, Ar and W are defined previously using a base such as $K_2CO_3$, or $Cs_2CO_3$ in solvents such as acetonitrile and toluene.

Two different methods were developed to make compounds of the type Formula 1, such as described in Examples 1-8. They were synthesized by attaching benzimidazole derivatives with 4-hydroxy-2-ethoxy phenyl propionic acid moiety as described in Schemes 3 and 4.

Scheme 4

A preferred group of compounds within the scope of Formula 1 are the carboxylic acids, i.e. those compounds where W is hydroxy. Formula 1 also includes certain compounds that are prodrugs of the carboxylic acid preferred group. Prodrugs, as utilized herein, are compounds that are converted to the claimed compounds as they are being administered to a patient or after they have been administered to a patient, are also included within the scope of the claimed active compounds. A non-limiting example of a prodrug of the preferred carboxylic acids of Formula 1 would be an ester of the carboxylic acid group, for example, a $C_1$-$C_6$ alkyl ester, wherein the alkyl portion may be linear or branched, or an ester which has functionality that makes it more easily hydrolyzed after administration to a patient.

Administration and Dosage Ranges

Any suitable route of administration may be employed for providing a mammal, especially a human, with an effective dose of a compound of the present invention. For example, oral, rectal, topical, parenteral, ocular, pulmonary, nasal, transdermal and the like may be employed. Dosage forms include tablets, troches, dispersions, suspensions, solutions, capsules, creams, ointments, aerosols, transdermal patches and the like. Preferably, compounds of Formula 1 are administered orally.

The effective dosage of active ingredient employed may vary depending on the particular compound employed, the mode of administration, the condition being treated and the severity of the condition being treated. Such dosage may be ascertained readily by a person skilled in the art in accordance with the following discussion.

When treating or preventing diabetes mellitus and/or hyperglycemia or hypertriglycemia or other diseases for which compounds of Formula 1 are indicated, generally satisfactory results are obtained when the compounds of the present invention are administered at a daily dosage of from about 0.1 mg-100 mg/kg of patient body weight, preferably given as a single daily dose, or in divided doses given 2-6 times/day, or via a sustained release dosage form. For larger mammals, including humans, the total daily dosage is from about 0.1 mg to 1 g, preferably from about 0.1-500 mg. In the case of 70 kg adult human, the total daily dose will generally be from about 0.7 mg to 350 mg. This dosage regimen may be adjusted to provide the optimal therapeutic response.

Pharmaceutical Compositions

Another aspect of the present invention provides pharmaceutical composition which comprises a compound of Formula 1 and a pharmaceutically acceptable carrier.

The compounds of Formula 1, its salts for various form of administration such as oral, nasal, parenteral and other as previously described, can be combined as the active ingredients in the admixture of a pharmaceutical carrier according to conventional pharmaceutical compounding techniques. The carrier may vary depending on the dosage form and chosen from the variety of the carriers such as water, glycols, oils, alcohols, flavoring agents, preservatives, coloring agents, sweetners and the like. Also carrier includes starches, sugars, cellulose, binders, and the like for hard and soft capsules or tablets and water, alcohol, glycerol, cellulose, oils and the like for solutions, dispersions or suspensions.

Combination Therapy

Compounds of Formula 1 may be used in combination with other drugs that may further enhance the optimal pharmaceutical properties thereof. The combination therapy may be used to further enhance the efficacy of treatment of a specific disease as described earlier, or to cover the broader area of the symptoms, or to lower the dosage of each therapeutic agent that must be administered or to enhance the pharmacokinetic properties of the therapy. The preferred effects are the enhancement of the efficacy for the treatment and control of disease and complications that accompany diabetes diseases.

Examples of other active ingredients that may be administered in combination with a compound of Formula 1 via separate administration or in a single pharmaceutical dosage form, include, but are not limited to:

(a) insulin sensitizers including (i) biguanides such as metformin and fenformin, (ii) PPARγ agonists such as pioglitazone, rosiglitazone and englitazone, (iii) protein tyrosine phosphatase-1B (PTP-1B) inhibitors and (iv) dipeptidyl peptidase IV inhibitors;
(b) insulin or insulin mimetics;
(c) sulfonylureas such as tolbutamide and glyburide;
(d) α-glucosidase inhibitors;

(e) cholesterol lowering agents such as HMG-CoA reductase inhibitors including lovastatin, simvastatin, pravastatin, fluvastatin, atorvastatin, itavastatin, rosuvestatin and rivastatin;
(f) cycloxygenase-2 (COX-2) inhibitors such as MBX-102;
(g) lipase inhibitors such as orlistat; and
(h) diuretics.

The invention further includes pharmaceutically acceptable compositions comprising any of the compounds described above and a pharmaceutically acceptable carrier.

The compounds of the present invention lower total cholesterol (TC); increase high density lipoprotein (HDL) and decrease low density lipoprotein (LDL), which have a beneficial effect on coronary heart disease and atherosclerosis.

The compounds of Formula 1 may be useful in reducing body weight and for the treatment and/or prophylaxis of diseases such as hypertension, coronary heart disease, atherosclerosis, stroke, peripheral vascular diseases and related disorders. The subject compounds may be useful for the treatment of familial hypercholesterolemia, hypertriglyceridemia, lowering of atherogenic lipoproteins, VLDL (very low density lipoprotein) and LDL. The compounds of the present invention can be used for the treatment of certain renal diseases including glomerulonephritis, glomerulosclerosis, nephrotic syndrome, hypertensive nephrosclerosis and nephropathy. The compounds of Formula 1 may also be useful for the treatment and/or prophylaxis of insulin resistance (type II diabetes), leptin resistance, impaired glucose tolerance, dyslipidemia, disorders related to syndrome X such as hypertension, obesity, insulin resistance, coronary heart disease and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, inflammation and for the treatment of cancer. The compounds of the present invention are useful in the treatment and/or prophylaxis of the above diseases in combination/con-comittant with one or more HMG CoA reductase inhibitors, hypolipidemic/hypolipoproteinemic agents such as fibric acid derivatives, nicotinic acid, cholestyramine, colestipol, and probucol.

The following examples are provided to illustrate the invention, including methods of making the compounds of the invention, and are not to be construed as limiting the invention in any manner. The scope of the invention is defined in the appended claims.

EXAMPLES

Specific examples of compounds of this invention are provided as Examples 1-7, listed by name below. There structures are illustrated in the Table 1.

TABLE 1

Specific examples of compounds of this invention

Example 1

TABLE 1-continued

Specific examples of compounds of this invention

Example 2

Example 3

Example 4

Example 5

Example 6

Example 7

Example 1

Preparation of 2-ethoxy-3-(4-{2-[2-(trifluoromethyl)-1H-benzimidazol-1-yl]ethoxy}phenyl)propanoic acid having following formula Step A: Preparation of ethyl 3-[4-(2-bromoethoxy)phenyl]-2-ethoxypropanoate having following formula Ethyl 2-ethoxy-3-(4-hydroxyphenyl)propanoate (2.38 g, 10 mmol) was dissolved in THF (20 ml) and triphenylphosphine (3.93 g, 15 mmol) was added followed by bromoethanol (1.06 ml, 15 mmol). The reaction mixture was cooled to 0° C. under $N_2$ atmosphere. DEAD(diethyl azodicarboxylate) (2.36 ml, 15 mmol) was added to the reaction mixture slowly over 10 minutes. After the completion of the reaction, the reaction mixture was stirred at 60° C. overnight. After the removal of solvent the residue was purified by column chromatography on silica gel using ethyl acetate and hexanes solvent system (1.96 g. 57%).

$^1$H NMR: (300 MHz, CDCl$_3$): δ 7.21 (t, 2H), 6.85 (t, 2H), 4.30 (t, 2H), 4.20 (t, 1H), 3.67-3.58 (m, 3H), 3.40-3.33 (m, 1H), 2.97 (t, 1H), 1.13-1.28 (m, 6H).

Mass m/z: 362.7 (M$^+$H$_2$O)

Step B: Preparation of ethyl 2-ethoxy-3-(4-{2-[2-(trifluoromethyl)-1H-benzimidazol-1-yl]ethoxy}phenyl)propanoate having following formula Ethyl 3-[4-(2-bromoethoxy)phenyl]-2-ethoxypropanoate (371 mg, 1 mmol) was dissolved in DMF (5 ml) and K$_2$CO$_3$ (552 mg, 4 mmol) was added followed by 2-trifluoromethyl benzimidazole (204 mg, 1.1 mmol). The reaction mixture was heated to 60° C. for 17 hrs. After the completion of the reaction, water was added and the product was extracted with Et$_2$O. The product was purified by column chromatography on silica gel using ethyl acetate and hexanes as solvent (333 mg, 70%).

$^1$H NMR: (300 MHz, CDCl$_3$): δ 7.92 (d, 1H), 7.68 (d, 1H), 7.53-7.40 (m, 2H), 7.14 (d, 2H), 6.73 (d, 1H), 4.46 (t, 2H), 4.34 (t, 2H), 4.18 (q, 2H), 3.95 (t, 1H), 3.63-3.60 (m, 1H), 3.58-3.31 (m, 1H), 2.95 (t, 2H), 1.26-1.14 (m, 6H).

Mass m/z: 451.7 (M$^+$H)

Step C: Preparation of 2-ethoxy-3-(4-{2-[2-(trifluoromethyl)-1H-benzimidazol-1-yl]ethoxy}phenyl) propanoic acid

To a stirred solution of ethyl 2-ethoxy-3-(4-{2-[2-(trifluoromethyl)-1H-benzimidazol-1-yl]ethoxy}phenyl)propanoate (238.5 mg, 0.5 mmol) in EtOH (5 ml) was added NaOH (2 ml, 2M aq. Solution, 2 mmol) in water (2 ml) at 0° C. at once. The reaction mixture was stirred at RT until all the ester disappeared (TLC). EtOH was removed in vacuo and the residue was dissolved in water. The solution was acidified to pH4 using 3N HCl and the precipitated acid was extracted with EtOAc to give the product as white solid (167 mg, 77.3%).

$^1$H NMR: (300 MHz, CDCl$_3$): δ. 7.90 (d, 1H), 7.67 (d, 1H), 7.51-7.37 (m, 2H), 7.13 (d, 2H), 6.73 (d, 2H), 4.75 (t, 2H), 4.33 (t, 2H), 4.03 (q, 1H), (3.63-3.57 (m, 1H), 3.45-3.40 (m, 1H), 3.09-2.90 (m, 2H), 1.17 (t, 3H).

Mass m/z: 423.5 (M$^+$H)

Example 2

Preparation of the compound 2-ethoxy-3-(4-{2-[2-(pentafluoroethyl)-1H-benzimidazol-1-yl]ethoxy}phenyl)propanoic acid having following formula Step A: Preparation of 2-(pentafluoroethyl)-1H-benzimidazole 1. To a stirred solution of o-nitro aniline (2.76 g, 20 mmol) and triethylamine (8.3 ml, 60 mmol) in CH$_2$Cl$_2$ (25 ml) was added pentafluoro propionic acid anhydride (9.7 ml, 50 mmol) at 0° C. under nitrogen atmosphere. After the completion of the addition, the reaction mixture was warmed to RT and stirred for 18 hrs. The reaction mixture was diluted with CH$_2$Cl$_2$ and washed successively with 1N.HCl and sat.NaHCO$_3$ and dried. The product was isolated after evaporation of the solvent (5.4 g, 95%).

$^1$H NMR: (300 MHz, CDCl$_3$): δ 11.54 (s, 1H), 8.78 (d, 1H), 8.35 (d, 1H), 7.79 (q, 1H), 7.40 (q, 1H).

2. 2,2,3,3,3-pentafluoro-N-(2-nitrophenyl)propanamide (5.37 g, 18.9 mmol) was dissolved in THF (15 ml) and 10% Pd/C (560 mg) was added. The solution was hydrogenated at 70 psi overnight. The catalyst was filtered on Celite™ and the solution was evaporated. The residue was dissolved in MeOH (50 ml) and Con.HCl (10 ml) was added and stirred for 12 hrs. After removing the solvents, the product was extracted with sat. NaHCO$_3$ and ethyl acetate. Upon evaporation of solvent, 2-(pentafluoroethyl)-1H-benzimidazole was isolated as pale yellow solid which was purified using column chromatography on silica gel using ethyl acetate and hexanes solvent system (4.1 g, 92%).

$^1$H NMR: (300 MHz, CDCl$_3$): δ 7.78-7.75 (m, 2H), 7.48-7.42 (m, 2H).

Mass m/z: 237.0 (M$^+$H)

Step B: Preparation of ethyl 2-ethoxy-3-(4-{2-[2-(pentafluoroethyl)-1H-benzimidazol-1-yl]ethoxy}phenyl)propanoate This compound was prepared from ethyl 3-[4-(2-bromoethoxy)phenyl]-2-ethoxypropanoate (371 mg, 1 mmol), 2-(pentafluoroethyl)-1H-benzimidazole (259 mg, 1.1 mmol), K$_2$CO$_3$ (552 mg, 4 mmol) and DMF (5 ml) using the procedure described in Step B of Example 1. Yield 420 mg (84%).

$^1$H NMR: (300 MHz, CDCl$_3$): δ 7.92 (d, 1H), 7.69 (d, 1H), 7.50 (t, 1H), 7.41 (t, 1H), 7.13 (d, 2H), 6.72 (d, 2H), 4.77 (t, 2H), 4.35 (t, 2H), 4.15 (q, 2H), 3.96-3.91 (m, 1H), 3.61-3.56 (m, 1H), 3.31 (d, 2H), 1.25-1.20 (m, 6H).

Mass m/z: 501.3 (M$^+$H)

Step C: Preparation of 2-ethoxy-3-(4-{2-[2-(pentafluoroethyl)-1H-benzimidazol-1-yl]ethoxy}phenyl)propanoic acid

The ethyl ester (200 mg, 0.4 mmol) from Step B was hydrolysed using NaOH (64 mg, 1.6 mmol) in ethanol (10 ml) and water (5 ml) by the procedure described in Step C of Example 1 (141 mg, 75%).

$^1$H NMR: (300 MHz, CDCl$_3$): δ 7.93 (d, 1H), 7.69 (d, 2H), 7.50 (t, 1H), 7.41 (t, 1H), 7.13 (d, 2H), 6.73 (d, 1H), 4.81-4.77 (brs, 1H), 4.35 (t, 2H), 4.03 (t, 2H), 4.03 (t, 1H), 3.62-3.57 (m, 1H), 3.46-3.40 (m, 1H), 3.08-2.91 (m, 2H), 1.16 (t, 3H).

Mass m/z: 473.1 (M$^+$H)

Example 3

Preparation of 3-(4-{2-[2,5-bis(trifluoromethyl)-1H-benzimidazol-1-yl]ethoxy}phenyl)-2-ethoxypropanoic acid having following formula Step A: Preparation of 2-{[2-nitro-4-(trifluoromethyl)phenyl]amino}ethanol To a stirred solution of 2-aminoethanol (5 ml, 150 mmol) in THF (20 ml), 1-fluoro-2-nitro-4-(trifluoromethyl)benzene (6.9 ml, 50 mmol) was added slowly at 0° C. After the completion of the addition, the reaction mixture was stirred at RT for 24 hrs. THF was evaporated using a rotary evaporator and the residue was extracted using water and ethyl acetate. Ethyl acetate was washed with more water, dried and evaporated to give crystalline 2-aminoethanol derivative (10.0 g, 80%).

$^1$H NMR: (300 MHz, CDCl$_3$): δ 8.53-8.49 (brs, 2H), 7.64 (d, 1H), 7.02 (d, 1H), 4.01 (t, 2H), 3.57 (t, 2H).

Step B: Preparation of 2-{[2-amino-4-(trifluoromethyl)phenyl]amino}ethanol

2-{[2-nitro-4-(trifluoromethyl)phenyl]amino}ethanol (3.05 g, 12 mmol) was dissolved in THF (10 ml) and hydrogenated at 70 psi. After the removal of catalyst the product was obtained by evaporating the solvent and used for the next step (2.70 g, 100%).

$^1$H NMR: (300 MHz, CDCl$_3$): δ 7.10 (d, 1H), 6.99 (s, 1H), 6.68 (d, 1H), 3.94 (t, 2H), 3.36 (t, 2H).

Mass m/z: 221.1 (M$^+$H)

Step C: Preparation of 2-[2,5-bis(trifluoromethyl)-1H-benzimidazol-1-yl]ethanol

A solution of 2-{[2-amino-4-(trifluoromethyl)phenyl]amino}ethanol (880 mg, 4 mmol), dimethylaminopyridine (488 mg, 4 mmol) and Et$_3$N (2.7 ml, 20 mmol) in CH$_2$Cl$_2$ (10 ml) was cooled to 0° C. under N$_2$ atmosphere. Trifluoroacetic anhydride (2.2 ml, 16 mmol) was added slowly to the reaction mixture. After the addition was complete, the reaction mixture was stirred at room temperature overnight. The reaction mixture was diluted with methylene chloride and washed with 1N HCl followed by saturated NaHCO$_3$ and dried. The solvent was evaporated and the residue was dissolved in 10 ml of methanol. Conc. HCl (2 ml) was added and stirred for 2 hrs and the solvents were evaporated. The product was extracted with ethyl acetate and dried. Ethyl acetate on evaporation gave the imidazole derivative obtained as solid (800 mg, 67%).

$^1$H NMR: (300 MHz, CDCl$_3$): δ 8.13 (s, 1H), 7.76-7.66 (m, 2H), 4.55 (t, 2H), 4.11 (t, 2H).

Mass m/z: 299.1 (M$^+$H)

Step D: Preparation of 2-[2,5-bis(trifluoromethyl)-1H-benzimidazol-1-yl]ethyl methanesulfonate To a stirred solution of 2-[2,5-bis(trifluoromethyl)-1H-benzimidazol-1-yl]ethanol (5.36 g, 17 mmol) in CH$_2$Cl$_2$ (15 ml), Et$_3$N (5.0 ml, 36 mmol) was added and cooled to 0° C. To the cooled solution, methanesulfonyl chloride (1.53 ml, 19.8 mmol) was added slowly.

After the completion of the addition, the reaction mixture was stirred at room temperature overnight. The reaction mixture was diluted with CH$_2$Cl$_2$ and washed with 1N.HCl followed by saturated NaHCO$_3$ and dried. The solvent was evaporated to give the product as pale yellow solid (5.44 g, 88%).

$^1$H NMR: (300 MHz, CDCl$_3$): δ 8.22 (s, 1H), 7.75 (t, 2H), 4.74 (t, 2H), 4.61 (t, 2H), 2.93 (s, 3H).

Mass m/z: 377.0 (M$^+$H)

Step E: Preparation of methyl 3-(4-{2-[2,5-bis(trifluoromethyl)-1H-benzimidazol-1-yl]ethoxy}phenyl)-2-ethoxypropanoate 2-[2,5-bis(trifluoromethyl)-1H-benzimidazol-1-yl]ethyl methanesulfonate (1.88 g, 5 mmol) and ethyl 2-ethoxy-3-(4-hydroxyphenyl)propanoate (1.19 g, 5 mmol) were taken in toluene (20 ml) and K$_2$CO$_3$ (1.38 g, 10 mmol) was added. The reaction mixture was heated under reflux for 30 hrs. Water was added to the reaction mixture and the product was extracted with ethyl acetate. The organic layer was dried and evaporated to the product which was purified by column chromatography on silica gel using ethyl acetate and hexanes as the solvent system (2.01 g, 77%).

$^1$H NMR: (300 MHz, CDCl$_3$): δ 8.21 (s, 1H), 7.84 (d, 1H), 7.74 (d, 1H), 7.13 (d, 2H), 6.71 (d, 2H), 4.71 (t, 2H), 4.35 (t, 2H), 4.17 (q, 2H), 3.95 (t, 1H), 3.60-3.48 (m, 1H), 3.35-3.20 (m, 1H), 2.84 (t, 2H), 1.23 (t, 3H), 1.15 (t, 3H).

Mass m/z: 519.2 (M$^+$H)

Step F: Preparation of 3-(4-{2-[2,5-bis(trifluoromethyl)-1H-benzimidazol-1-yl]ethoxy}phenyl)-2-ethoxypropanoic acid

The ethyl ester from Step E was hydrolysed according to the procedure described in Step C of Example 1 (3.78 g, 91%).

$^1$H NMR: (300 MHz, CDCl$_3$): δ 8.19 (s, 1H), 7.84 (d, 1H), 7.74 (d, 1H), 7.14 (d, 2H), 6.72 (d, 2H), 4.79 (t, 2H), 4.35 (t, 2H), 4.04 (t, 1H), 3.62-3.57 (m, 1H), 3.47-3.42 (m, 1H), 3.03-2.96 (m, 2H), 1.16 (t, 3H).

Mass m/z: 491.1 (M$^+$H)

Example 4

Preparation of 3-(4-{2-[5-fluoro-2-(trifluoromethyl)-1H-benzimidazol-1-yl]ethoxy}phenyl)-2-ethoxypropanoic acid having following formula Step A: Preparation of 2-[(4-fluoro-2-nitrophenyl)amino]ethanol This compound was prepared from 1,4-difluoro-2-nitrobenzene (21.8 ml, 100 mmol) and 2-amino ethanol (10 ml, 300 mmol) using analogous procedure described in Step A of Example 3. Yield (19.2 g, 96%).

$^1$H NMR: (300 MHz, CDCl$_3$): δ 8.14 (brs, 1H), 7.94-7.88 (m, 1H), 7.31-7.25 (m, 1H), 6.91 (dd, 1H), 3.97 (t, 2H), 3.52 (t, 2H).

Step B: Preparation of 2-[(2-amino-4-fluorophenyl)amino]ethanol

Nitro compound (4.98 g, 24.9 mmol) from step A was dissolved in 10 ml of THF and Pd (C) 10% (480 mg) was added and hydrogenated at 70 PSI overnight. The catalyst was filtered and washed with THF. The THF was evaporated to give the amino compound (4.74 g, 99%).

$^1$H NMR: (300 MHz, CDCl$_3$): δ 6.63-6.58 (m, 1H), 6.50-6.44 (m, 2H), 3.85 (mt, 2H), 3.30 (brs, 2H), 3.21 (t, 2H).

Mass m/z: 171.1 (M$^+$H)

Step C: Preparation of 2-[5-fluoro-2-(trifluoromethyl)-1H-benzimidazol-1-yl]ethanol This compound was prepared from 2-[(2-amino-4-fluorophenyl)amino]ethanol and trifluroacetic anhydride using analogous procedure described in Step C of Example 3.

Yield (5.60 g, 84%).

$^1$H NMR: (300 MHz, CDCl$_3$): δ 7.56 (q, 1H), 7.45 (q, 1H), 7.25-7.18 (m, 1H), 4.49 (t, 2H), 4.08 (t, 2H).

Mass m/z: 249.1 (M$^+$H)

Step D: Preparation of 2-[5-fluoro-2-(trifluoromethyl)-1H-benzimidazol-1-yl]ethyl methanesulfonate This compound was prepared using a procedure analogous to that described in Step D of Example 3.

Yield (2.40 g, 92%).

$^1$H NMR: (300 MHz, CDCl$_3$): δ 7.59-7.52 (m, 2H), 7.31-7.24 (m, 1H), 4.71 (t, 2H), 4.58 (t, 2H), 2.90 (s, 3H).

Mass m/z: 327.1 (M$^+$H)

Step E: Preparation of ethyl 3-(4-{2-[5-fluoro-2-(trifluoromethyl)-1H-benzimidazol-1-yl]ethoxy}phenyl)-2-ethoxypropanoate This compound was prepared using a procedure analogous to that described in Step E of Example 3.

Yield (1.50 g, 80%).

$^1$H NMR: (300 MHz, CDCl$_3$): δ 7.64 (q, 1H), 7.54 (q, 1H), 7.26-7.25 (m, 1H), 7.11 (d, 2H), 6.71 (d, 2H), 4.73 (t, 2H), 4.32 (t, 2H), 4.17 (q, 2H), 3.94 (t, 1H), 3.62-3.57 (m, 1H), 3.35-3.30 (m, 1H), 2.94 (t, 2H), 1.23 (t, 3H), 1.16 (t, 3H).

Mass m/z: 469.3 (M$^+$H)

Step F: Preparation of 3-(4-{2-[5-fluoro-2-(trifluoromethyl)-1H-benzimidazol-1-yl]ethoxy}phenyl)-2-ethoxypropanoic acid

The ethyl ester from Step E was hydrolysed according to the procedure described in Step C of Example 1 (1.10 g, 83%).

$^1$H NMR: (300 MHz, CDCl$_3$): δ 7.64 (q, 1H), 7.55 (q, 1H), 7.26-7.22 (m, 1H), 713 (d, 2H), 6.73 (d, 2H), 4.74 (t, 2H), 4.33 (t, 2H), 4.05 (t, 1H), 4.02-3.43 (m, 2H), 3.06-2.96 (d, 2H).

Mass m/z: 441.1 (M$^+$H)

Example 5

Preparation of 3-(4-{2-[5-phenyl-2-(trifluoromethyl)-1H-benzimidazol-1-yl]ethoxy}phenyl)-2-ethoxypropanoic acid having following formula Step A: Preparation of ethyl 3-(4-{2-[5-phenyl-2-(trifluoromethyl)-1H-benzimidazol-1-yl]ethoxy}phenyl)-2-ethoxypropanoate Ethyl-3-(4-{2-[5-bromo-2-(trifluoromethyl)-1H-benzimidazol-1-yl]ethoxy}phenyl)-2-ethoxypropanoate (529 mg, 1 mmol), PPh$_3$ (3.93 mg, 0.015 mmol), Pd(OAc)$_2$ (1.3 mg, 0.006 mmol) and PhB(OH)$_2$ (142 mg, 1.2 mmol) were mixed in n-propanol (5 ml). Na$_2$CO$_3$ (212 mg, 2 mmol) was dissolved in water (2.5 ml) and added to the mixture. The reaction mixture was refluxed under N$_2$ atmosphere for 4 hrs and cooled. The solvents were evaporated and the residue was dissolved in ethyl acetate and passed through a small pad of silica. The silica was washed with additional ethyl acetate. Solvent was evaporated to give the product which was purified by HPLC (243 mg, 46%).

$^1$H NMR: (300 MHz, CDCl$_3$): δ 8.15 (s, 1H), 7.75 (s, 2H), 7.68 (d, 2H), 7.42 (t, 2H), 7.40-7.38 (m, 1H), 7.12 (d, 2H), 6.73 (d, 2H), 4.78 (t, 2H), 4.38 (t, 2H), 4.03 (t, 1H), 3.63-3.57 (m, 1H), 3.45-3.40 (m, 1H), 3.05-2.96 (m, 2H), 1.15 (t, 3H).

Mass m/z: 527.2 (M$^+$H)

Step B: Preparation of 3-(4-{2-[5-phenyl-2-(trifluoromethyl)-1H-benzimidazol-1-yl]ethoxy}phenyl)-2-ethoxypropanoic acid

The ethyl ester from Step A was hydrolysed according to the procedure described in Step C of Example 1 (39.2 mg, 79%).

$^1$H NMR: (300 MHz, CDCl$_3$): δ 8.13 (s, 1H), 7.75 (s, 2H), 7.67 (d, 2H), 7.42 (t, 2H), 7.40-7.38 (m, 1H), 7.14 (d, 2H), 6.75 (d, 2H), 4.78 (t, 2H), 4.35 (t, 2H), 4.03 (t, 1H), 3.63-3.57 (m, 1H), 3.45-3.40 (m, 1H), 3.05-2.96 (m, 2H), 1.15 (t, 3H)

Mass m/z: 499.1 (M$^+$H)

Example 6

Preparation of (2S)-3-{4-[2-(2-trifluoromethyl-benzoimidazol-1-yl)-ethoxy]-phenyl}-2-ethoxy-propionic acid having following formula Step A: Preparation of 2-Ethoxy-N-(2-hydroxy-1-phenyl-ethyl)-3-{4-[2-(2-trifluoromethyl-benzoimidazol-1-yl)-ethoxy]-phenyl}-propionamide having the following formula 2-Ethoxy-3-(4-{2-[2-(trifluoromethyl)-1H-benzimidazol-1-yl]ethoxy}phenyl)propanoic acid (6.33 g, 15 mmol) was dissolved in 20 ml of dichloromethane and cooled to 5° C. 4.16 ml (30 mmol) of Et$_3$N was added and stirred for 10 min. (S)-phenyl glycinol (2.26 g, 16.5 mmol) and Et$_3$N (4.16 ml, 30 mmol) were dissolved in 20 ml of dichloromethane and this solution was added to the reaction mixture and stirred at RT overnight. The reaction mixture was diluted with CH$_2$Cl$_2$ and washed with water followed by dil.HCl and sat. NaHCO$_3$. The dichloromethane layer was dried and evaporated to give a mixture of amides (8.6 g) which were separated by column chromatography using ethyl acetate and hexanes over silica gel to afford two different diastereomers. First eluting diastereomer was tentatively assigned as [2R, N(1S)]-3-{4-[2-(2-trifluoromethyl-benzoimidazol-1-yl)-ethoxy]-phenyl}-2-ethoxy-N-(2-hydroxy-1-phenylethyl)propionamide following the similar precedents by Braj B. Lohray et al [J. Of Med. Chem., 2001, 44, 2675-2678] and 2$^{nd}$ eluting diastereomer was assigned as [2S, N(1S)]-3-{4-[2-(2-trifluoromethyl-benzoimidazol-1-yl)-ethoxy]-phenyl}-2-ethoxy-N-(2-hydroxy-1-phenylethyl)propionamide.

First eluting diastereomer ([2R, N(1S)]-3-{4-[2-(2-trifluoromethyl-benzoimidazol-1-yl)-ethoxy]-phenyl}-2-ethoxy-N-(2-hydroxy-1-phenylethyl)propionamide): Yield: 3.06 g (37.7%)

R$_f$=0.38 (hex:EtOAc=1:1)

$^1$H NMR: (300 MHz, CDCl$_3$): δ 7.90 (d, 1H), 7.69 (d, 1H), 7.46-7.40 (m, 2H), 7.37-7.30 (m, 4H), 7.15 (d, 2H), 7.03 (d, 1H), 6.75 (d, 2H), 4.98-4.96 (m, 1H), 4.75 (t, 2H), 4.34 (t, 2H), 3.95 (q, 1H), 3.68 (d, 2H), 3.47 (q, 2H), 3.07 (d, 1H), 2.94 (d, 1H), 1.25 (t, 3H).

Mass m/z: 542.2 (M$^+$H)

2$^{nd}$ eluting diastereomer (First eluting diastereomer ([2S, N(1S)]-3-{4-[2-(2-trifluoromethyl-benzoimidazol-1-yl)-ethoxy]-phenyl}-2-ethoxy-N-(2-hydroxy-1-phenylethyl)propionamide)): Yield: 2.6 g (32.0%)

R$_f$=0.15 (hex:EtOAc=1:1)

$^1$H NMR: (300 MHz, CDCl$_3$): δ 7.95 (d, 1H), 7.73 (d, 1H), 7.38-7.55 (m, 2H), 7.18-7.6.95 (m, 8H), 7.66 (d, 2H), 4.98-4.97 (m, 1H), 4.77 (t, 2H), 4.30 (t, 2H), 3.98 (q, 1H), 3.85 (d, 2H), 3.58-3.51 (m, 1H), 3.07 (d, 1H), 2.90 (d, 1H), 2.40 (brs, 1H) 1.25 (t, 3H).

Mass m/z: 542.2 (M$^+$H)

Step B: Preparation of (2S)-3-{4-[2-(2-trifluoromethyl-benzoimidazol-1-yl)-ethoxy]-phenyl}-2-ethoxy-propionic acid The 2nd eluting amide from the previous step (2.6 g, 4.8 mmol) was dissolved in dioxane (100 ml) and 1N H$_2$SO$_4$ (97 ml) was added and the reaction mixture was refluxed under N$_2$ atmosphere for 4 days. Dioxane was removed and to the rest of the solution was added 20 ml of sat. NaHCO$_3$. Ether (30 ml) was added and the organic impurities were taken into the ether layer. The aqueous phase was acidified and the precipitated acid was extracted with ethyl acetate. The organic layer was dried and evaporated to give the product as pale yellow gum. The acid was purified by recrystallization with ether/hexane mixture.

Yield: 1.16 g (57.3%)

$^1$H NMR: (300 MHz, CDCl$_3$): δ. 7.90 (d, 1H), 7.67 (d, 1H), 7.51-7.37 (m, 2H), 7.13 (d, 2H), 6.73 (d, 2H), 4.75 (t, 2H), 4.33 (t, 2H), 4.03 (q, 1H), (3.63-3.57 (m, 1H), 3.45-3.40 (m, 1H), 3.09-2.90 (m, 2H), 1.17 (t, 3H).

Mass m/z: 423.3 (M$^+$H)

Example 7

Preparation of (2R)-3-{4-[2-(2-trifluoromethyl-benzoimidazol-1-yl)-ethoxy]-phenyl}-2-ethoxy-propionic acid having following formula From 3.0 g of the 1$^{st}$ eluting diastereomer from Example 6, 1.6 g (49.7%) of (2R)-3-{4-[2-(2-trifluoromethyl-benzoimidazol-1-yl)-ethoxy]-phenyl}-2-ethoxy-propionic acid was similarly prepared.

$^1$H NMR: (300 MHz, CDCl$_3$): δ. 7.90 (d, 1H), 7.67 (d, 1H), 7.51-7.37 (m, 2H), 7.13 (d, 2H), 6.73 (d, 2H), 4.75 (t, 2H), 4.33 (t, 2H), 4.03 (q, 1H), (3.63-3.57 (m, 1H), 3.45-3.40 (m, 1H), 3.09-2.90 (m, 2H), 1.17 (t, 3H).

Mass m/z: 423.3 (M$^+$H)

Example 8

Biological Assays

The transcription factor PPARs (peroxisome proliferator-activated receptor) are members of the nuclear receptor gene family and has three subtypes: PPAR-α, PPAR-δ(β), and PPAR-γ. These receptors modulate metabolic risk factors for cardiovascular disease associated with metabolic syndromes including glucose homeostasis, insulin resistance, dyslipidemia and hypertension, which together are known as the metabolic syndrome X. The recent development of a novel class of insulin sensitizing drugs called thiazolidinediones (TZDs) is a good example of the use of PPAR-γ receptor in the treatment of type II diabetes. This correlation facilitated the search for better PPAR agonist drugs. In addition to this PPAR-γ action, fibrates are known drug classes that are effective at lowering serum triglyceride and increasing HDL cholesterol. These findings have increased the interest in developing dual activators due to the additional lipid control afforded by the PPAR-α. Although less is known about the third PPAR subtype, the recent published data on the selective PPAR-δ agonist (GW501516) that showed decreased triglyceride along with VLDL and LDL cholesterol and raised HDL cholesterol in obese monkeys provided a unique opportunity to develop a dual or even triple activators as promising drug candidates for the treatment of these complicated metabolic syndromes. The compound of Example 1 was tested for in vitro glucose uptake, transactivation, and also in vivo blood glucose, insulin, lipid lowering activities in different experimental animal models.

a) Insulin-Stimulated Glucose Uptake

Figure 1:
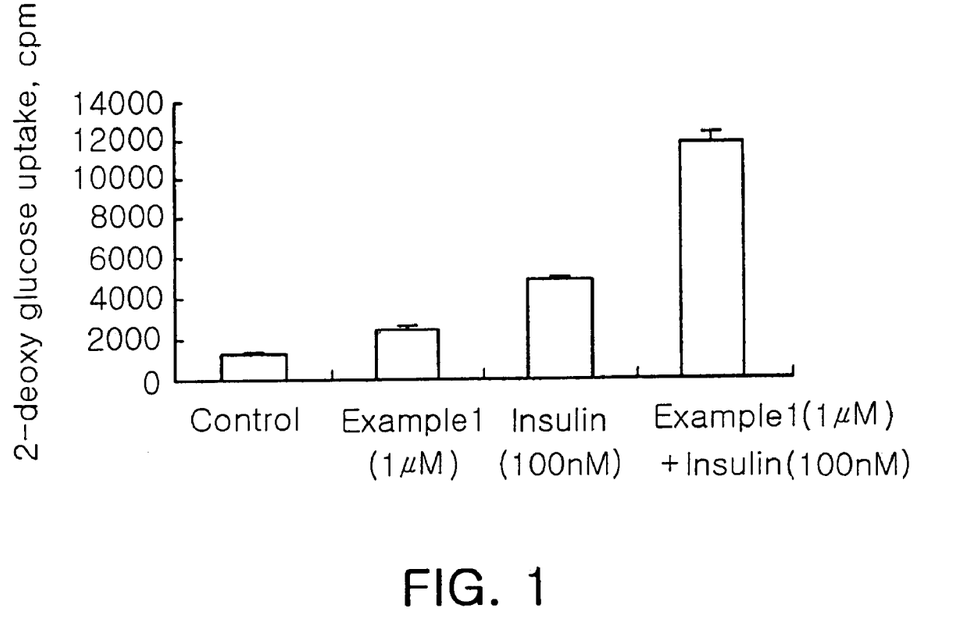
FIG. 1 illustrates an effect of compound of this invention (1 μM) on 2-deoxy-D-glucose uptake in the presence of 100 nM of insulin.

3T3-L1 fibroblasts (American Type Culture Collection) were plated and grown for 2 days postconfluence in Dulbecco's modified Eagle's medium (DMEM; 4,500 mg/L glucose, HyClone) supplemented 10% FBS, 10 μg/mL penicillin and streptomycin in an atmosphere of 5% CO$_2$ at 37° C. Adipocyte differentiation was then induced using standard protocol. After 48 hours, the differentiation medium was replaced with maintenance medium containing DMEM supplemented with 10% FBS. The maintenance medium was changed every 3 days until the cells were utilized for experimentation. Glucose transport activity was measured in the presence or absence of insulin and the protocol was modified from Kletzien, R F et al. (1992) Molecular Pharmacology 41:393-398. Briefly, differentiated 3T3-L1 adipocytes were incubated with control (DMSO), insulin (100 nM) alone, the compound of Example 1 (1 μM) alone and a combination of insulin (100 nM)+the compound of Example 1 (1 μM) for 48 h. In each instance, the medium was changed twice a day. Glucose uptake was measured using 2-Deoxy-D-[1-$^3$H] glucose as label after 90 min incubation with each compound. The separate treatment of 1 μM of the compound of Example 1 and 100 nM of insulin showed the increase in glucose transport. However, glucose transport activity was significantly increased by the addition of 1 μM of the compound of Example 1 in the presence of 100 nM of insulin as shown in FIG. 1 indicating a synergistic effect of this compound.

b) Transactivation

For the transactivation assay, GAL4 fusions were made by fusing human PPARα, δ and γ ligand binding domain to the C-terminal end of yeast GAL4 DNA binding domain of pM1 vector. The stable-PPAR-reporter-assay 3T3 (SPRAT) cell lines have been produced using a plasmid vector containing a selectable gene marker for the antibiotic Gentacin. The SPRAT cells for PPARs were propagated in Dulbecco's modified Eagle's medium supplemented with 10% fetal calf serum (Gibco BRL), 0.2 mg/ml streptomycin, 200 U/ml penicillin and 0.4 mg/ml Gentacin. Following expansion to confluence in flasks, the cells were split into 96 well plates. Addition of the compound of Example 1 was performed using a liquid handling robot (BioMek 2000) with the highest concentration being 100 μM, final. The cells were placed in the incubator at 37° C. for 6 hours. Subsequently, the Bright-Glo luciferase assay system (Promega, Madison Wis.) was employed. And the plates read immediately in a Molecular Devices Analyst AD system. The EC$_{50}$ value for each compound was determined using GraphPad Prism.

TABLE 1

| In Vitro hPPAR-α, hPPAR-γ and hPPAR-δ Transactivation | | | | | | |
|---|---|---|---|---|---|---|
| | PPAR-α | | PPAR-γ | | PPAR-δ | |
| | EC$_{50}$ (μM) | % Max | EC$_{50}$ (μM) | % Max | EC$_{50}$ (μM) | % Max |
| Cmpd of Ex 1 | 17.2 | 44 | 0.04 | 62 | 50 | 68 |
| Reference (α) | 0.07 | 100 | — | — | — | — |
| Rosiglitazone (γ) | — | — | 0.04 | 100 | — | — |
| TTA (δ) | — | — | — | — | 38 | 100 | c) Stereoselectivity of Compound 1

Figure 2:
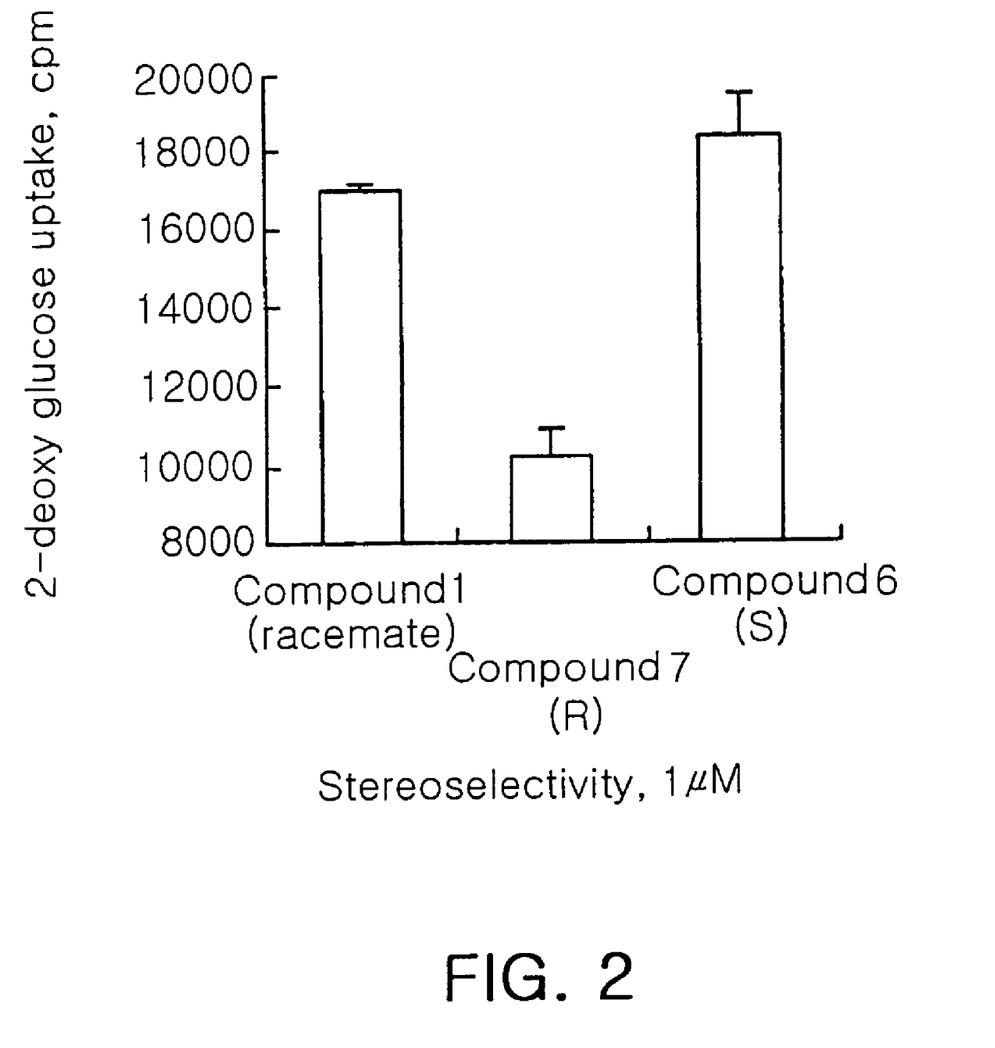
FIG. 2 illustrates an effect of each enantiomer and racemate on insulin-stimulated glucose uptake.

In order to determine whether there is an enantio-dependency of compound of example 1, we investigated the effect of each enantiomer and racemate on insulin-stimulated glucose uptake as described above. The enantio-dependency was noted and (S)-compound (Example 6) exhibited a statistically significant difference (P<0.01) over racemate (Example 1) and the R-enantiomer (Example 7) as shown in FIG. 2.

d) Efficacy Test for Blood Glucose and Plasma Lipid Lowering (db/db Mice)

Mice used in this study were standard model of type II diabetes developed by Jackson Laboratories (Bar Harbor, Me.). Mice (male, 8-wk-old db/db) were housed six per cage in hanging wire bottom cages with standard laboratory conditions. The mice had free access to normal chow (Purina Rodent Chow) and water. At the age of 8-10 weeks, the mice were bled from the tail for glucose matching among the groups (n=6 per group). To test the PPAR-γ effect of the compounds of Examples 1, 2, 3, 4 and 6, mice were then dosed orally with vehicle (CMC) or with two different concentrations (3 or 10 mg/kg/d) of each compound for 7-14 days. Each compound of Examples 1, 2, 3, 4 and 6 was dosed as suspension in 0.5% CMC+0.2% Tween 80 in sterile water. Fresh suspension was prepared for 8 days dosing and kept in a refrigerator. The suspension was administered orally by gavage daily in the morning. The control group received vehicle (dose 10 mL/kg). Blood glucose concentrations (in fed state) were monitored at basal and 3 h post dose on day 14 either by putting a drop of blood from tails on a glucose strip for analysis by a glucometer or using a 10 μL plasma sample in a YSI (Yellow Spring Instruments, OH) analyzer. Additional blood was collected in EDTA tubes and centrifuged at 4,000×g for 10 min at 4° C. and plasma samples were analyzed for insulin, TG and free fatty acid. The results are expressed in Table 2 as % maximal reduction that is achieved relative to vehicle treated control group. Animals having more than 300 mg/dL of blood glucose were used for testing. Statistical significance (* P<0.05; ** P<0.01) is given versus the appropriate sample in vehicle treated animals.

TABLE 2

In Vivo Efficacy in Male db/db Mice After Oral Treatment for 7-14 Days

| Compound (Example No.) | Dose mg/kg | BG % max reduction d14 | Insulin % max reduction d7/d14 | TG % max reduction d14 | Fatty Acid % max reduction d14 |
|---|---|---|---|---|---|
| 1 | 3 | 69** | 85** (d7) | 52** | 47** |
|   | 10 | 73** | 87** (d7) | 55** | 72** |
| 2 | 3 | 57** | 59** (d14) | 50** | 45** |
|   | 10 | 75** | 75** (d14) | 70** | 71** |
| 3 | 3 | 77** | 76** (d14) | 61** | 49** |
|   | 10 | 77** | 79** (d14) | 77** | 76** |
| 4 | 3 | 68** | 79** (d14) | 64** | 25** |
|   | 10 | 73** | 79** (d14) | 58** | 27** |
| 6 | 3 | 53** | 87** (d7) | 62** | 54** |
|   | 10 | 73** | 86** (d7) | 66** | 60** |

All the compounds tested greatly decreased blood glucose levels with 14-days treatment and resulted in normalization (data not shown) of the hyperglycemia and a concomitant reduction in insulin levels either at day 7 or at day 14 in a dose-related manner, indicating markedly increased insulin sensitivity. In addition to normalizing blood glucose, test compounds also showed a dose related reduction of non-fasted plasma TG and FFA levels.

e) Oral Glucose Tolerance Test (OGTT)

Figure 3:
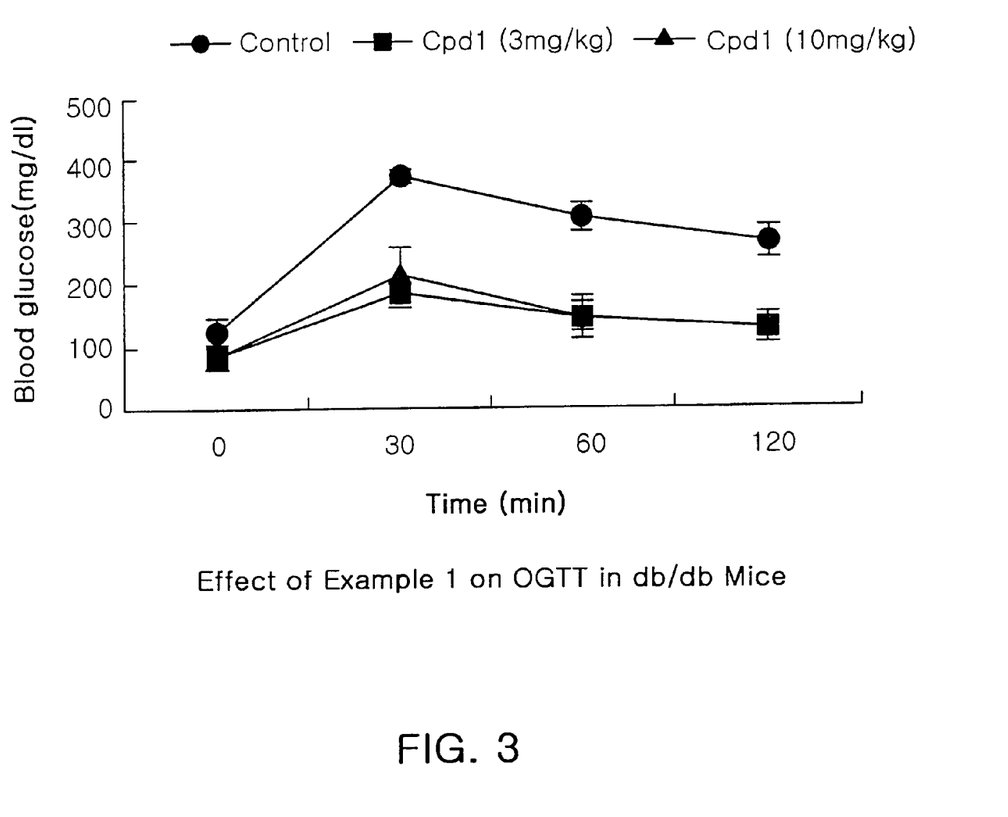
FIG. 3 illustrates an effect of compound of this invention on Oral Glucose Tolerance Test in db/db Mice.

OGTT was performed in db/db mice after dosing of either 3 or 10 mg/kg of the compound of Example 1 for 9 days. The animals were dosed with 10% glucose in water in a volume of 10 mL/kg. Blood samples were taken at 0, 30, 60 and 120 min post dose. The results are shown in FIG. 3. The AUC measured for blood glucose was significantly reduced by 49% and 48% in groups with 3 and 10 mg/kg of Example 1, respectively when compared to vehicle control.

Since the compound of Example 1 activated PPAR-α and δ along with its PPAR-γ activity in an in vitro transactivation assay, we performed the following in vivo experiments using human ApoA1 transgenic mouse and high cholesterol-fed rat models to assure these effects.

f) Effect of the Compound of Example 1 on the Changes in Plasma ApoA1, HDL Cholesterol and TG Levels (Human ApoA1 Transgenic Mice)

Homozygous human ApoA1 transgenic mouse strains (C57BL/6-TgN1Rub) were purchased from Jackson Laboratories (Bar Harbor, Me.). The mice were grouped by six and housed in hanging wire bottom cages with standard laboratory conditions. The mice had free access to normal chow (Purina Rodent Chow) and water. The grouped mice were then dosed orally with vehicle (CMC) or with different concentrations of the compound of Example 1 (3, 10 or 30 mg/kg/d) for 8 days. Compounds were dosed as suspension in 0.5% CMC+0.2% Tween 80 in sterile water. Fresh suspension was prepared for 8 days dosing and kept in a refrigerator. The suspension was administered orally by gavage daily in the morning. The control group received vehicle (dose 10 mL/kg). Blood samples were collected by cardiac puncture, centrifuged and analyzed for ApoA1, HDL cholesterol, and triglyceride. The results are shown in Table 3.

TABLE 3

Effect of Example 1 on Changes in Cholesterol Levels in Human ApoA1 Transgenic Mice

| Compound | ApoA1 % increase | HDL Cholesterol % increase | TG % decrease |
|---|---|---|---|
| Example 1 (3 mg/kg) | 52 | 47* | 52* |
| Example 1 (10 mg/kg) | 137 | 73** | 56** |
| Example 1 (30 mg/kg) | 186 | 51** | 67** |

**$P < 0.01$;
*$P < 0.05$

The data from human ApoA1 transgenic mice, a mechanistic model to demonstrate ApoA1 dependent HDL-cholesterol modulation upon PPAR-α/δ activation, clearly showed that the compound of Example 1 greatly increased HDL-cholesterol through the increase in human ApoA1 levels.

g) Effect of the Compound of Example 1 on the Changes in Plasma Lipid Parameters (High Cholesterol-fed Rats)

Male Sprague-Dawley rats (6 wks, Charles River) were fed on a high cholesterol diet (1.25% cholesterol, 0.5% cholic acid, Research Diets Inc. C13002) ad libitum for 10 days. To estimate the in vivo PPAR-α effect, rats (N=6) were dosed orally by gavage in a volume of 10 mL/kg with the compound of Example 1 (10 mg/kg/d) prepared as suspension in vehicle (0.5% CMC+0.2% Tween 80 in sterile water) for 4 days. Blood was collected and analyzed for non-fasted total cholesterol and free fatty acid levels. The results are calculated as the percent reduction relative to vehicle control. The results are shown in Table 4.

TABLE 4

Effect of Example 1 on Changes in Cholesterol Levels in High Cholesterol Fed Rats After Oral Treatment for 4 Days

| Compound | Total Cholesterol % reduction | Free Fatty Acid % reduction |
|---|---|---|
| Example 1 (10 mg/kg) | 69** | 68** |
| Rosiglitazone (10 mg/kg) | 19 | +13 |

**$P < 0.01$

As expected, plasma total cholesterol and free fatty acid levels were significantly reduced with the administration of the compound of Example 1, but not with same dose level of rosiglitazone, suggesting that PPAR-γ activation was not responsible for plasma lipid regulation.

What is claimed is:

1. A compound represented by structural Formula 1:

Formula 1 wherein $R_1$, $R_2$, $R_3$ and $R_4$ are independently selected from hydrogen, hydroxy, halogen, nitro, $C_{1-7}$alkyl, —$OC_{1-7}$alkyl, $C_{1-7}$ haloalkyl, —$OC_{1-7}$ haloalkyl, —$SO_2C_{1-7}$alkyl, —$SO_2NR_aR_b$, —$SO_2$phenyl, —$OSO_2C_{1-7}$ alkyl, —$C(O)C_{1-7}$ alkyl, —COphenyl and phenyl, wherein the phenyl groups are unsubstituted or substituted with 1-3 substituents independently selected from halogen, —$C_{1-7}$alkyl, —$C_{1-7}$haloalkyl, —$OC_{1-7}$alkyl, and —$OC_{1-7}$ haloalkyl; or adjoining pairs of $R_{1-4}$, together with that portion of the ring to which they are attached, form a partially saturated or unsaturated 5-8 member cyclic ring containing from 0-4 heteroatoms independently selected from N, O and S, said ring is unsubstituted or independently substituted with 1-3 halogens and 1-4 $C_{1-7}$alkyl groups;

$R_5$ is selected from hydrogen, $C_{1-7}$ alkyl, —$OC_{1-7}$ alkyl, —Ophenyl, —$SO_2C_{1-7}$ alkyl, —$SO_2$ phenyl, —$C(O)C_{1-3}$ alkyl, —$C(O)$phenyl, —$C(O)OC_{1-3}$ alkyl, —$CF_3$, —$CF_2CF_3$ and —$C(O)NR_aR_b$, wherein the phenyl groups are unsubstituted or substituted with one to three substituents independently selected from halogen, —$C_{1-7}$alkyl, —$C_{1-7}$haloalkyl, —$OC_{1-7}$alkyl and —$OC_{1-7}$haloalkyl;

$R_6$ and $R_6'$ are independently selected from hydrogen, halogen, $C_{1-7}$alkyl, —$C_{1-7}$ haloalkyl, hydroxy, —$OC_{1-7}$ alkyl, —$OC_{1-7}$ haloalkyl and phenyl wherein the phenyl group is unsubstituted or substituted with one to three substituents independently selected from halogen, —$C_{1-7}$alkyl, —$C_{1-7}$haloalkyl, —$OC_{1-7}$alkyl and —$OC_{1-7}$haloalkyl;

$R_7$ is selected from hydrogen, halogen, $C_{1-7}$ alkyl, $C_{1-7}$ haloalkyl and phenyl wherein the phenyl group is unsubstituted or substituted with one to three substituents independently selected from halogen, —$C_{1-7}$ alkyl, —$C_{1-7}$ haloalkyl, —$OC_{1-7}$ alkyl and —$OC_{1-7}$ haloalkyl;

$R_8$ is selected from H, $C_{1-7}$ alkyl, $C_{1-7}$ haloalkyl and phenyl wherein the phenyl group is unsubstituted or substituted with one to three substituents independently selected from halogen, —$C_{1-7}$alkyl, —$C_{1-7}$haloalkyl, —$OC_{1-7}$ alkyl and —$OC_{1-7}$haloalkyl;

Ar is a 6-10 membered monocyclic or bicyclic ring system divalent linking group that is unsubstituted or substituted with 1-5 substituents independently selected from halogen, $C_{1-7}$ alkyl, $C_{1-7}$ haloalkyl, —$OC_{1-7}$ alkyl, $OC_{1-7}$ haloalkyl and phenyl, wherein the phenyl group is unsubstituted or substituted with one to three substituents independently selected from halogen, —$C_{1-7}$alkyl, —$C_{1-7}$haloalkyl, —$OC_{1-7}$alkyl and —$OC_{1-7}$haloalkyl;

X is a divalent linking group selected from =O, =$CR_aR_b$, =S, =$NR_a$, =CO and =$SO_2$;

n is an integer from 1-6;

W is selected from the group of consisting of hydroxy, —$OR_c$, —$NR_cR_d$ and —$NR_cSO_2R_e$;

each of $R_a$ and $R_b$ is independently hydrogen or $C_{1-7}$alkyl;

each of $R_c$ and $R_d$ is independently hydrogen, $C_{1-7}$alkyl and $C_{1-7}$haloalkyl;

$R_e$ is selected from the group consisting of hydrogen, —$C_{1-7}$ alkyl, —$C_{1-7}$ haloalkyl and phenyl wherein the phenyl group is unsubstituted or substituted with one to three substituents independently selected from halogen, —$C_{1-7}$alkyl, —$C_{1-7}$haloalkyl, —$OC_{1-7}$alkyl and —$OC_{1-7}$haloalkyl;

the asterisk represents an asymmetric carbon atom;

each alkyl group is either linear or branched-chain;

enriched enantiomers thereof and pharmaceutically acceptable salts thereof.

2. A compound in accordance with claim 1, wherein said compound is represented by Formula 2:

Formula 2 wherein $R_1$, $R_2$, $R_3$ and $R_4$ are independently selected from the group consisting of hydrogen, $C_{1-7}$ alkyl, halogen, —$OC_{1-5}$ alkyl, —$OC_{1-5}$ haloalkyl and phenyl which is unsubstituted or substituted with 1-3 groups independently selected from halogen, $C_{1-5}$ alkyl, $C_{1-5}$ haloalkyl, —$OC_{1-3}$ alkyl and —$OC_{1-3}$ haloalkyl, or adjoining pairs of $R_{1-4}$, together with that portion of the ring to which they are attached, form a partially saturated or unsaturated 5-8 member cyclic ring, said ring being unsubtituted or substituted with 1-3 halogens or 1-4 $C_{1-7}$ alkyl groups; $R_5$ is selected from the group consisting of —$CF_3$, —$CF_2CF_3$, —$SO_2Me$, —COMe and —$CO_2Me$; $R_8$ is selected from the group consisting of methyl, ethyl, n-propyl, iso-propyl, and —$CH_2CF_3$; the asterisk represents an asymmetric carbon atom; and pharmaceutically acceptable salts thereof.

3. A compound in accordance with claim 1, represented by Formula 3:

Formula 3 wherein $R_1$ through $R_4$ are independently selected from the group consisting of hydrogen, $C_{1-7}$ alkyl, halogen, $C_{1-5}$ haloalkyl and phenyl which is unsubstituted or substituted with 1-3 groups independently selected from halogen, $C_{1-5}$ alkyl, C$_{1-5}$ haloalkyl, —OC$_{1-3}$ alkyl and C$_{1-5}$ haloalkyl, with the proviso that at least two of R$_1$ through R$_4$ are hydrogen; R$_5$ is —CF$_3$, —CF$_2$CF$_3$, —SO$_2$Me, —COMe and —CO$_2$Me; R$_8$ is selected from the group consisting of methyl, ethyl, n-propyl, iso-propyl, and —CH$_2$CF$_3$; the asterisk represents an asymmetric carbon atom; and pharmaceutically acceptable salts thereof.

4. A compound in accordance with claim 1, wherein R$_1$, R$_2$, R$_3$, and R$_4$ are independently selected from the group consisting of hydrogen, chloro, fluoro, —CF$_3$, CF$_2$CF$_3$, C$_{1-4}$ alkyl, C$_{1-4}$ haloalkyl, —SO$_2$Me and phenyl which is unsubstituted or substituted with 1-3 substituents independently selected from halogen, methyl, ethyl, propyl, isopropyl, methoxy, ethoxy, n-propoxy, isopropoxy, —CF$_3$ and —OCF$_3$.

5. A compound in accordance with claim 4, wherein R$_1$, R$_2$, R$_3$, and R$_4$ are independently selected from the group consisting of hydrogen, fluoro, —CF$_3$ and —SO$_2$Me.

6. A compound in accordance with claim 5, wherein R$_1$, R$_2$, R$_3$, and R$_4$ are hydrogen.

7. A compound in accordance with claim 1, wherein R$_5$ is selected from the group of hydrogen, methyl, ethyl, CF$_3$, CF$_2$CF$_3$, methoxy, phenoxy, —SO$_2$Me, —SO$_2$Ph, —COMe, and —C(O)Ph, wherein the phenyl groups are unsubstituted or substituted with 1-3 substituents independently selected from halogen, methyl, ethyl, propyl, isopropyl, methoxy, ethoxy, n-propoxy, isopropoxy, —CF$_3$ and —OCF$_3$.

8. A compound in accordance with claim 7, wherein R$_5$ is selected from the group of —CF$_3$, —CF$_2$CF$_3$, —SO$_2$Me, —COMe and —CO$_2$Me.

9. A compound in accordance with claim 8, wherein R$_5$ is selected from the group of —CF$_3$, and —CF$_2$CF$_3$ and n is 2.

10. A compound in accordance with claim 1, wherein said compound is in the (S) enantiomeric form in the substantial absence of the (R) enantiomeric form.

11. A compound in accordance with claim 2, wherein said compound is in the (S) enantiomeric form in the substantial absence of the (R) enantiomeric form.

12. A compound in accordance with claim 3, wherein said compound is in the (S) enantiomeric form in the substantial absence of the (R) enantiomeric form.

13. A compound in accordance with claim 1, wherein X is selected from the group consisting of =O, =S and =SO$_2$.

14. A compound in accordance with claim 1, wherein Ar is unsubstituted or substituted with from 1-5 substituents independently selected from the group consisting of halogen, methyl, ethyl, propyl, methoxy, ethoxy, propoxy and —OCF$_3$.

15. A compound in accordance with claim 1, wherein R$_6$ and R$_6$' are selected from the group of hydrogen, fluoro, methyl, ethyl, phenyl, methoxy and ethoxy.

16. A compound in accordance with claim 1, wherein R$_7$ is selected from the group of hydrogen, fluoro, methyl, ethyl and phenyl.

17. A compound in accordance with claim 1, wherein R$_8$ is selected from the group of hydrogen, methyl, ethyl, n-propyl, isopropyl, n-butyl, isobutyl, sec-butyl, tert-butyl, phenyl, —CF$_3$, —CF$_2$CF$_3$, and —CH$_2$CF$_3$.

18. A compound in accordance with claim 17, wherein R$_8$ is selected from the group of ethyl, isopropyl, —CH$_2$CF$_3$, and phenyl.

19. A compound in accordance with claim 1, wherein W is selected from the group of OH, methoxy, ethoxy, amino, —NHMe, —NMe$_2$, —NHSO$_2$Me and —NHSO$_2$Ph.

20. A compound in accordance with claim 1, wherein R$_6$, R$_6$' and R$_7$ are hydrogen.

21. A compound in accordance with claim 1, wherein R$_1$, R$_2$, R$_3$, R$_4$, R$_6$, R$_6$' and R$_7$ are each hydrogen, R$_8$ is ethyl, W is hydroxy, R$_5$ is —CF$_3$, n is 2, X is O and the asterisk represents an asymmetric carbon atom, said compound having the structural formula

22. A compound in accordance with claim 21, wherein said compound is in the (S) enantiomeric form in the substantial absence of the (R) enantiomeric form.

23. A compound in accordance with claim 1, wherein the compound of the Formula 1 is selected from those compounds represented by the following structures:

-continued

24. A method of treating or controlling one or more diseases, disorders, or conditions selected from the group consisting of (1) non-insulin dependent diabetes mellitus (NIDDM), (2) hyperglycemia, (3) impaired glucose tolerance, (4) insulin resistance, (5) obesity, (7) disorders, (7) dyslipidemia, (8) hyperlipodemia, (9) hypertriglyceridemia, (10) hypercholesterolemia, (11) low HDL levels, (12) high LDL levels and (13) atherosclerosis, said method comprising the administration of an effective amount of a compound represented by structural Formula 1:

Formula 1 wherein $R_1$, $R_2$, $R_3$ and $R_4$ are independently selected from hydrogen, hydroxy, halogen, nitro, $C_{1-7}$alkyl, —$OC_{1-7}$ alkyl, $C_{1-7}$ haloalkyl, —$OC_{1-7}$ haloalkyl, —$SO_2C_{1-7}$alkyl, —$SO_2NR_aR_b$, —$SO_2$phenyl, —$OSO_2C_{1-7}$alkyl, —C(O)$C_{1-7}$ alkyl, —COphenyl and phenyl, wherein the phenyl groups are unsubstituted or substituted with 1-3 ubstituents independently selected from halogen, —$C_{1-7}$ alkyl, —$C_{1-7}$ haloalkyl, —$OC_{1-7}$ alkyl, and —$OC_{1-7}$ haloalkyl; or adjoining pairs of $R_{1-4}$, together with that portion of the ring to which they are attached, form a partially saturated or unsaturated 5-8 member cyclic ring containing from 0-4 heteroatoms independently selected from N, O and S, said ring is unsubstituted or independently substituted with 1-3 halogens and 1-4 $C_{1-7}$alkyl groups;

$R_5$ is selected from hydrogen, $C_{1-7}$ alkyl, —$OC_{1-7}$ alkyl, —Ophenyl, —$SO_2C_{1-7}$ alkyl, —$SO_2$ phenyl, —C(O)$C_{1-3}$ alkyl, —C(O)phenyl, —C(O)$OC_{1-3}$ alkyl, —$CF_3$, —$CF_2CF_3$ and —C(O)$NR_aR_b$, wherein the phenyl groups are unsubstituted are substituted with one to three substituents independently selected from halogen, —$C_{1-7}$alkyl, —$C_{1-7}$haloalkyl, —$OC_{1-7}$alkyl and —$OC_{1-7}$haloalkyl;

$R_6$ and $R_6'$ are independently selected from hydrogen, halogen, $C_{1-7}$alkyl, —$C_{1-7}$haloalkyl, hydroxy, —$OC_{1-7}$ alkyl, —$OC_{1-7}$ haloalkyl and phenyl wherein the phenyl group is unsubstituted or substituted with one to three subsituents independently selected from halogen, —$C_{1-7}$alkyl, —$C_{1-7}$haloalkyl, —$OC_{1-7}$alkyl and —$OC_{1-7}$haloalkyl;

$R_7$ is selected from hydrogen, halogen, $C_{1-7}$alkyl, $C_{1-7}$haloalkyl and phenyl wherein the phenyl group is unsubstituted or substituted with one to three substituents independently selected from halogen, —$C_{1-7}$alkyl, —$C_{1-7}$haloalkyl, —$OC_{1-7}$alkyl and —$OC_{1-7}$ haloalkyl;

$R_8$ is selected from H, $C_{1-7}$ alkyl, $C_{1-7}$ haloalkyl and phenyl wherein the phenyl group is unsubstituted or substituted with one to three substituents independently selected from halogen, —$C_{1-7}$alkyl, —$C_{1-7}$haloalkyl, —$OC_{1-7}$ alkyl and —$OC_{1-7}$haloalkyl; p1 Ar is a 6-10 membered monocyclic or bicyclic ring stem divalent linking group that is unsubstituted or substituted with 1-5 substituents independently selected from halogen, $C_{1-7}$ alkyl, $C_{1-7}$ haloalkyl, —$OC_{1-7}$ alkyl, $OC_{1-7}$ haloalkyl and phenyl, wherein the phenyl group is unsubstituted or substituted with one to three substituents independently selected from halogen, —$C_{1-7}$alkyl, —$C_{1-7}$haloalkyl, —$OC_{1-7}$ alkyl and —$OC_{1-7}$haloalkyl;

X is a divalent linking group selected from =O, =$CR_aR_b$, =S, =$NR_a$, =CO and =$SO_2$;

n is an integer from 1-6;

W is selected from the group consisting of hydroxy, —$OC_c$, —$NR_cR_d$ and —$NR_cSO_2R_e$;

each of $R_a$ and $R_b$ is independently hydrogen or $C_{1-7}$alkyl;

each of $R_c$ and $R_d$ is independently hydrogen, $C_{1-7}$alkyl and $C_{1-7}$haloalkyl;

$R_e$ is selected from the group consisting of hydrogen, —$C_{1-7}$ alkyl, —$C_{1-7}$ haloalkyl and phenyl wherein the phenyl group is unsubstitute or substituted with one to three substituents independently selected from halogen, —$C_{1-7}$alkyl, —$C_{1-7}$haloalkyl, —$OC_{1-7}$alkyl and —$OC_{1-7}$haloalkyl;

the asterisk represents an asymmetric carbon atom;

each alkyl group is either linear or branched-chain;

enriched enantiomers thereof and pharmaceutically acceptable salts thereof.

25. A method in accordance with claim 24, wherein said disease, disorder or condition is non-insulin dependent (Type II) diabetes mellitus.

26. A method in accordance with claim 25, wherein said compound of-Formula 1 is in the (S) enantiomeric form in the substantial absence of the (R) enantiomeric form.

27. A method in accordance with claim 24, wherein said disease, disorder or condition is hyperglycemia.

28. A method in accordance with claim 24, wherein said disease, disorder or condition is hyperlipidemia or low HDL.

29. A method in accordance with claim 24, wherein said disease, disorder or condition is obesity.

30. A method in accordance with claim 24, wherein said disease, disorder or condition is hypercholesterolemia.

31. A method in accordance with claim 24, wherein said disease, disorder or condition is hypertriglyceridemia.

32. A method in accordance with claim 24, wherein said disease, disorder or condition is dyslipidemia.

33. A method in accordance with claim 24, wherein said disease, disorder or condition is atherosclerosis.

34. A method of treating, controlling one or more diseases, disorders, or conditions selected from the group in claim 24, where insulin resistance is a component thereof, said method comprising the administration of an effective amount of said compound of Formula 1 and an effective amount of one or more to the compounds selected from the group consisting of:

(a) an insulin sensitizer including (i) biguanides metformin and fenformin, (ii) PPARγ agonist including pioglitazone, rosiglitazone and englitazone, (iii) protein tyrosine phosphatase-1B (PTP-1B) inhibitors and (iv) dipeptidyl peptidase IV inhibitors;

(b) insulin;
(c) a sulfonylureas including tolbutamide and glyburide;
(d) a cholesterol lowering agent including a HMG-CoA reductase inhibitor;
(e) a cyclooxygenase-2 (COX-2) inhibitor including MBX-102;
(f) a lipase inhibitor including orlistat; and
(g) a diuretic.

35. A method in accordance with claim 34, wherein said compound of Formula 1 is in the (S) enantiomeric form in the substantial absence of the (R) enantiomeric form.

36. A method in accordance with claim 34, wherein said disease, disorder or condition is atherosclerosis and said compound administered with a compound of Formula 1 is an HMG-CoA reductase inhibitor.

37. The method as recited in claim 36, wherein said HMG-CoA reductase inhibitor is selected from the group consisting of simvistatin, lovastatin, pravastatin, fluvastatin, atorvastatin, itavastatin rosuvestatin an rivastatin.

* * * * *